United States Patent
Abdou

(10) Patent No.: US 8,303,660 B1
(45) Date of Patent: Nov. 6, 2012

(54) INTER-VERTEBRAL DISC PROSTHESIS WITH VARIABLE ROTATIONAL STOP AND METHODS OF USE

(76) Inventor: Samy Abdou, San Diego, CA (US)

( * ) Notice: Subject to any disclaimer, the term of this patent is extended or adjusted under 35 U.S.C. 154(b) by 1368 days.

(21) Appl. No.: 11/739,053

(22) Filed: Apr. 23, 2007

Related U.S. Application Data

(60) Provisional application No. 60/793,790, filed on Apr. 22, 2006.

(51) Int. Cl.
*A61F 2/44* (2006.01)
(52) U.S. Cl. ................................. 623/17.14; 623/17.15
(58) Field of Classification Search ..... 623/17.11–17.16
See application file for complete search history.

(56) References Cited

U.S. PATENT DOCUMENTS

| | | | |
|---|---|---|---|
| 4,759,769 A | 7/1988 | Hedman et al. | |
| 4,997,432 A | 3/1991 | Keller | |
| 5,011,484 A | 4/1991 | Breard | |
| 5,092,866 A | 3/1992 | Breard et al. | |
| 5,180,393 A | 1/1993 | Commarmond | |
| 5,387,213 A | 2/1995 | Breard | |
| 5,425,773 A | 6/1995 | Boyd et al. | |
| 5,514,180 A | 5/1996 | Heggeness et al. | |
| 5,540,688 A | 7/1996 | Navas | |
| 5,556,431 A * | 9/1996 | Buttner-Janz | 623/17.15 |
| 5,562,737 A | 10/1996 | Graf | |
| 5,562,738 A * | 10/1996 | Boyd et al. | 623/17.15 |
| 5,620,169 A | 4/1997 | Payne | |
| 5,672,175 A | 9/1997 | Martin | |
| 5,674,294 A | 10/1997 | Bainville et al. | |
| 5,674,296 A | 10/1997 | Bryan et al. | |
| 5,676,701 A | 10/1997 | Yuan et al. | |
| 5,725,582 A | 3/1998 | Bevan et al. | |
| 5,888,226 A | 3/1999 | Rogozinski | |
| 5,961,516 A | 10/1999 | Graf | |
| 5,976,186 A | 11/1999 | Bao et al. | |
| 5,984,923 A | 11/1999 | Breard | |
| 6,001,130 A | 12/1999 | Bryan et al. | |
| 6,019,792 A | 2/2000 | Cauthen | |
| 6,022,376 A | 2/2000 | Assell et al. | |
| 6,093,205 A | 7/2000 | McLeod et al. | |
| 6,146,044 A | 11/2000 | Calvet | |
| 6,162,252 A | 12/2000 | Kuras et al. | |

(Continued)

FOREIGN PATENT DOCUMENTS

WO    WO-2007-095333      8/2007

(Continued)

OTHER PUBLICATIONS

Denis, F., "The Three Column Spin and its Significance in the Classification of acute thoracolumbar spinal injuries" *Spine* Nov.-Dec. 1983; 8(8):817-831.

*Primary Examiner* — Alvin Stewart
*Assistant Examiner* — Jerry Cumberledge
(74) *Attorney, Agent, or Firm* — Gazdzinski & Associates, PC

(57) ABSTRACT

A prosthesis is adapted for implantation into the spine. The prosthesis has a first member and a second member. The first member and the second member have a permitted range of rotational motion with respect to one another. The amount of permitted rotation of the first member relative to the second member is dependant on the extent of flexion and extension of the spine.

20 Claims, 12 Drawing Sheets

U.S. PATENT DOCUMENTS

| | | | |
|---|---|---|---|
| 6,179,873 B1 * | 1/2001 | Zientek | 623/17.11 |
| 6,248,106 B1 | 6/2001 | Ferree | |
| 6,296,643 B1 | 10/2001 | Hopf | |
| 6,348,071 B1 | 2/2002 | Steffee et al. | |
| 6,355,038 B1 | 3/2002 | Pisharodi | |
| 6,368,350 B1 | 4/2002 | Erickson et al. | |
| 6,419,706 B1 | 7/2002 | Graf | |
| 6,440,168 B1 | 8/2002 | Cauthen | |
| 6,461,358 B1 | 10/2002 | Faccioli et al. | |
| 6,461,359 B1 | 10/2002 | Tribus et al. | |
| 6,482,234 B1 | 11/2002 | Weber et al. | |
| 6,520,996 B1 | 2/2003 | Manasas et al. | |
| 6,527,803 B1 * | 3/2003 | Crozet et al. | 623/17.11 |
| 6,540,785 B1 | 4/2003 | Gill et al. | |
| 6,592,624 B1 | 7/2003 | Fraser et al. | |
| 6,607,558 B2 | 8/2003 | Kuras | |
| 6,610,093 B1 | 8/2003 | Pisharodi | |
| 6,645,207 B2 | 11/2003 | Dixon et al. | |
| 6,645,249 B2 | 11/2003 | Ralph et al. | |
| 6,666,612 B2 | 12/2003 | Lorigny et al. | |
| 6,673,113 B2 | 1/2004 | Ralph et al. | |
| 6,679,915 B1 | 1/2004 | Cauthen | |
| 6,682,530 B2 | 1/2004 | Dixon et al. | |
| 6,706,068 B2 | 3/2004 | Ferree | |
| 6,709,461 B2 | 3/2004 | O'Neil et al. | |
| 6,723,127 B2 | 4/2004 | Ralph et al. | |
| 6,749,635 B1 | 6/2004 | Bryan | |
| 6,758,861 B2 | 7/2004 | Ralph et al. | |
| 6,764,515 B2 | 7/2004 | Ralph et al. | |
| 6,770,096 B2 | 8/2004 | Bolger et al. | |
| 6,966,910 B2 | 11/2005 | Ritland | |
| 7,083,622 B2 | 8/2006 | Simonson | |
| 7,083,649 B2 | 8/2006 | Zucherman et al. | |
| 7,101,399 B2 | 9/2006 | Errico et al. | |
| 7,128,761 B2 | 10/2006 | Kuras et al. | |
| 7,204,853 B2 | 4/2007 | Gordon et al. | |
| 7,273,496 B2 | 9/2007 | Mitchell | |
| 7,316,714 B2 | 1/2008 | Gordon et al. | |
| 7,331,995 B2 | 2/2008 | Eisermann et al. | |
| 7,594,932 B2 | 9/2009 | Aferzon et al. | |
| 7,695,517 B2 * | 4/2010 | Benzel et al. | 623/17.15 |
| 7,727,280 B2 * | 6/2010 | McLuen | 623/17.16 |
| 7,749,274 B2 * | 7/2010 | Razian | 623/17.16 |
| 7,799,081 B2 | 9/2010 | McKinley | |
| 8,038,716 B2 * | 10/2011 | Duggal et al. | 623/17.14 |
| 2001/0039452 A1 | 11/2001 | Zucherman et al. | |
| 2003/0065395 A1 | 4/2003 | Ralph et al. | |
| 2003/0078662 A1 | 4/2003 | Ralph et al. | |
| 2003/0176923 A1 | 9/2003 | Keller et al. | |
| 2003/0199981 A1 * | 10/2003 | Ferree | 623/17.15 |
| 2003/0208273 A1 | 11/2003 | Eisermann et al. | |
| 2003/0217809 A1 | 11/2003 | Morishige | |
| 2004/0049280 A1 | 3/2004 | Cauthen | |
| 2004/0143264 A1 | 7/2004 | McAfee | |
| 2004/0143332 A1 * | 7/2004 | Krueger et al. | 623/17.14 |
| 2004/0220670 A1 | 11/2004 | Eisermann et al. | |
| 2004/0225364 A1 | 11/2004 | Richelsoph et al. | |
| 2004/0225365 A1 | 11/2004 | Eisermann et al. | |
| 2004/0225366 A1 | 11/2004 | Eisermann et al. | |
| 2004/0236329 A1 | 11/2004 | Panjabi | |
| 2004/0236425 A1 | 11/2004 | Huang | |
| 2004/0243240 A1 | 12/2004 | Beaurain et al. | |
| 2004/0267369 A1 | 12/2004 | Lyons et al. | |
| 2005/0033431 A1 | 2/2005 | Gordon et al. | |
| 2005/0043800 A1 | 2/2005 | Paul et al. | |
| 2005/0043802 A1 | 2/2005 | Eisermann et al. | |
| 2005/0071007 A1 | 3/2005 | Malek | |
| 2005/0125066 A1 | 6/2005 | McAfee | |
| 2005/0149196 A1 * | 7/2005 | Zucherman et al. | 623/17.14 |
| 2005/0165487 A1 | 7/2005 | Muhanna et al. | |
| 2005/0171543 A1 | 8/2005 | Timm et al. | |
| 2005/0171608 A1 | 8/2005 | Peterman et al. | |
| 2005/0171609 A1 | 8/2005 | Humphreys et al. | |
| 2005/0171610 A1 | 8/2005 | Humphreys et al. | |
| 2005/0177156 A1 | 8/2005 | Timm et al. | |
| 2005/0192671 A1 | 9/2005 | Bao et al. | |
| 2005/0197702 A1 | 9/2005 | Coppes et al. | |
| 2005/0216083 A1 | 9/2005 | Michelson | |
| 2005/0222682 A1 | 10/2005 | Link et al. | |
| 2005/0234555 A1 | 10/2005 | Sutton et al. | |
| 2005/0240273 A1 | 10/2005 | Khandkar et al. | |
| 2005/0256576 A1 | 11/2005 | Moskowitz et al. | |
| 2005/0283241 A1 | 12/2005 | Keller et al. | |
| 2006/0069436 A1 * | 3/2006 | Sutton et al. | 623/17.13 |
| 2006/0069438 A1 * | 3/2006 | Zucherman et al. | 623/17.14 |
| 2006/0084988 A1 | 4/2006 | Kim | |
| 2006/0085076 A1 * | 4/2006 | Krishna et al. | 623/17.15 |
| 2006/0106395 A1 | 5/2006 | Link et al. | |
| 2006/0116768 A1 | 6/2006 | Krueger et al. | |
| 2006/0178746 A1 | 8/2006 | Bartish, Jr. et al. | |
| 2006/0190082 A1 | 8/2006 | Keller et al. | |
| 2006/0195192 A1 | 8/2006 | Gordon et al. | |
| 2006/0217809 A1 | 9/2006 | Albert et al. | |
| 2006/0276900 A1 | 12/2006 | Carpenter | |
| 2007/0021836 A1 | 1/2007 | Doty | |
| 2007/0161992 A1 | 7/2007 | Kwak et al. | |
| 2007/0162133 A1 | 7/2007 | Doubler et al. | |
| 2007/0191958 A1 | 8/2007 | Abdou | |
| 2007/0282448 A1 | 12/2007 | Abdou | |
| 2008/0015698 A1 | 1/2008 | Marino | |
| 2008/0027550 A1 * | 1/2008 | Link et al. | 623/17.16 |
| 2008/0039843 A1 | 2/2008 | Abdou | |
| 2008/0281358 A1 | 11/2008 | Abdou | |
| 2010/0087858 A1 | 4/2010 | Abdou | |

FOREIGN PATENT DOCUMENTS

| | | |
|---|---|---|
| WO | WO-2007-140382 | 12/2007 |
| WO | WO-2008-021319 | 2/2008 |
| WO | WO-2008-073447 | 6/2008 |

* cited by examiner

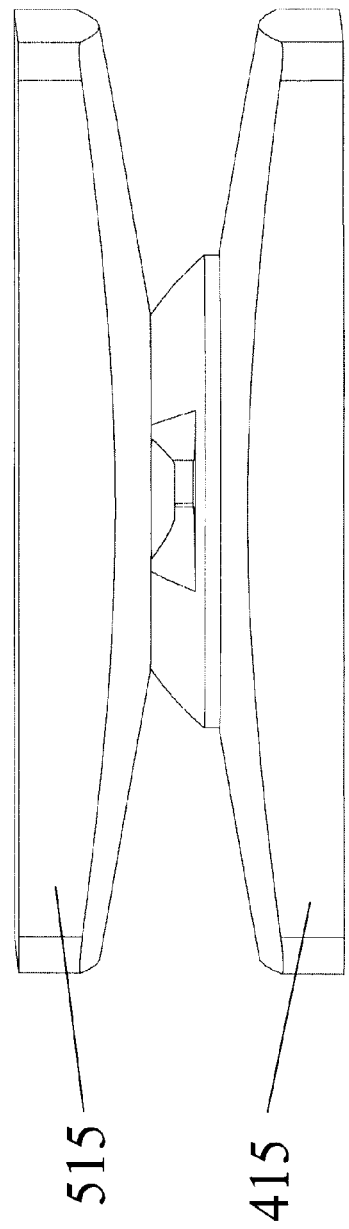
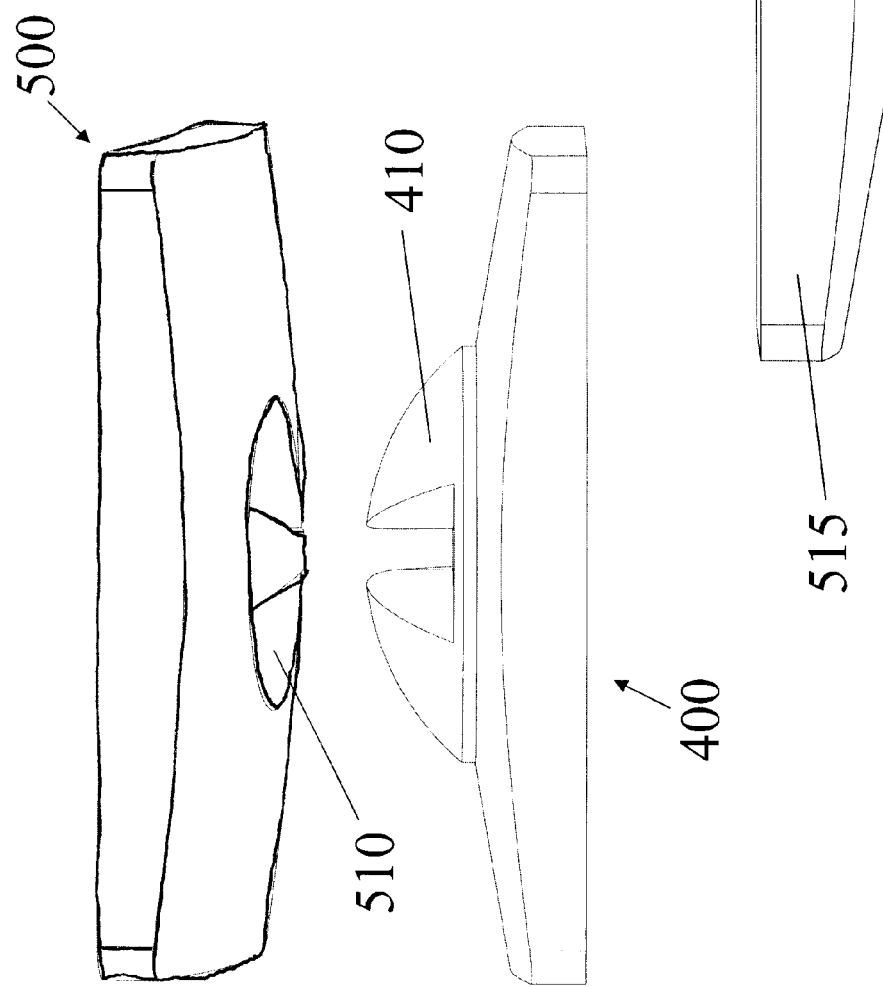
Fig. 1

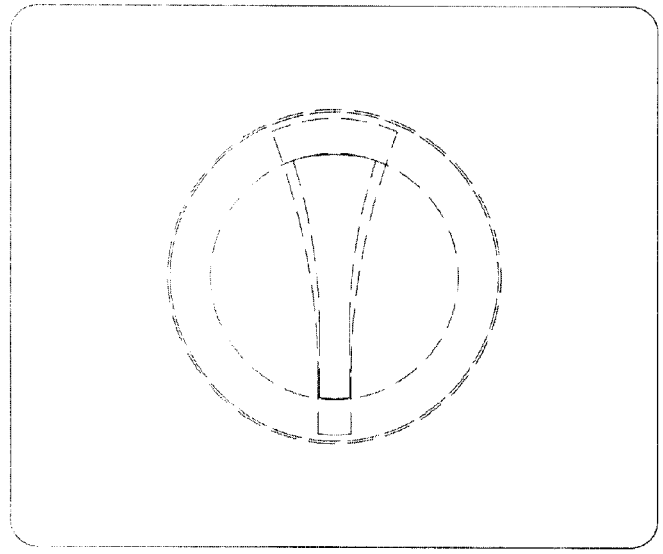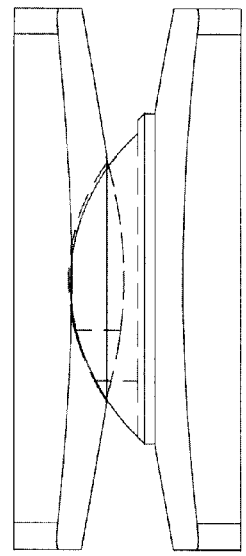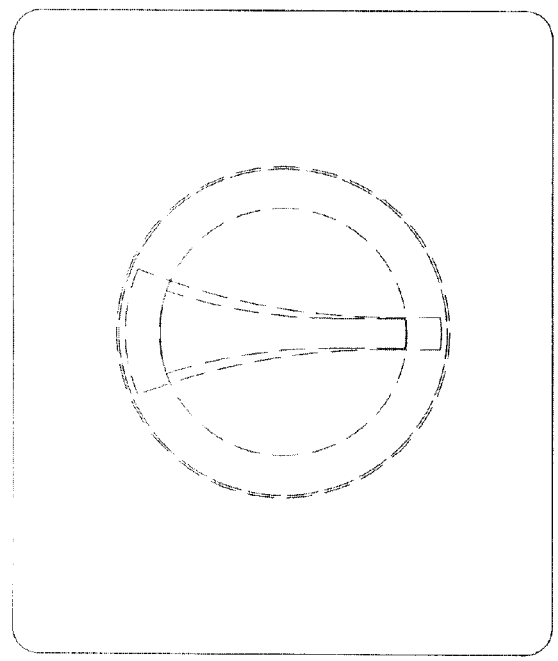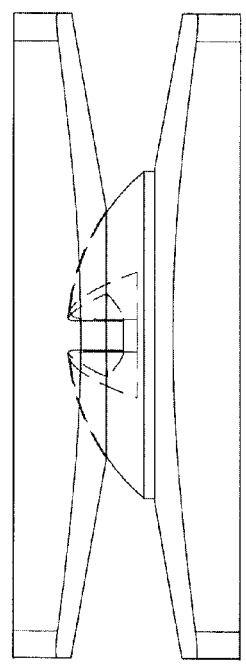
Fig. 3

Fig. 4
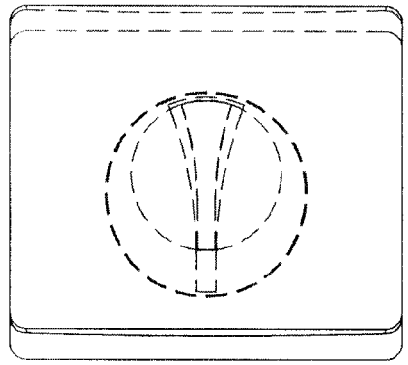
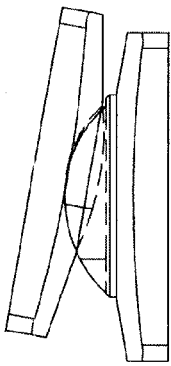
A
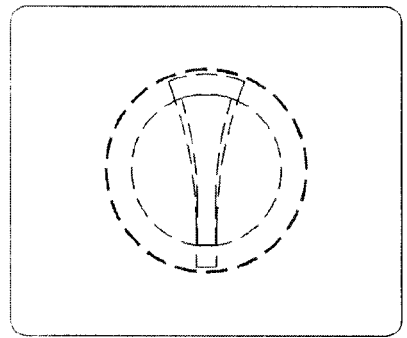
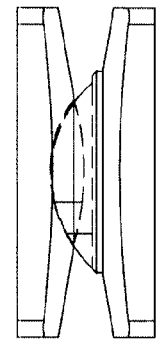
B
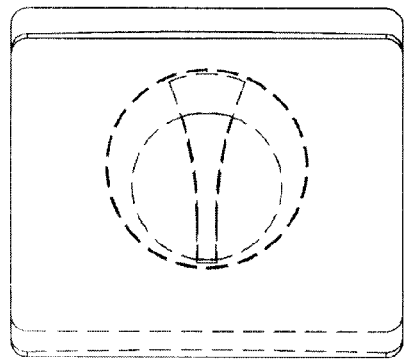
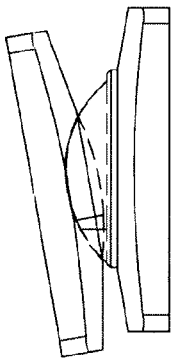
C

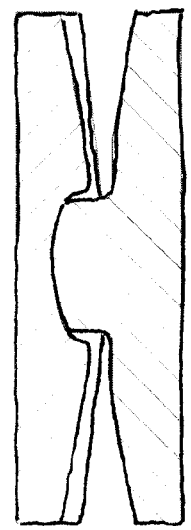 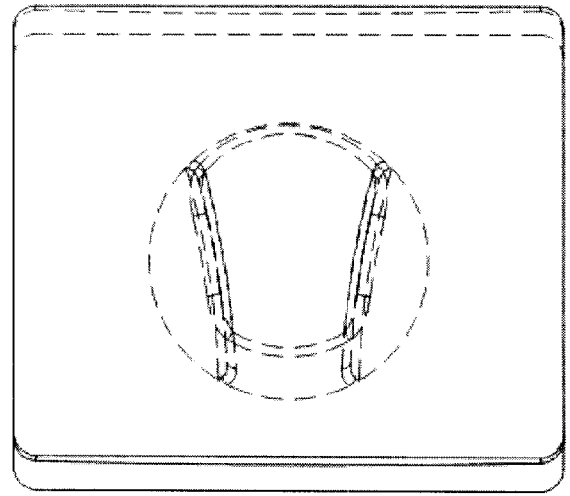
Fig. 6A
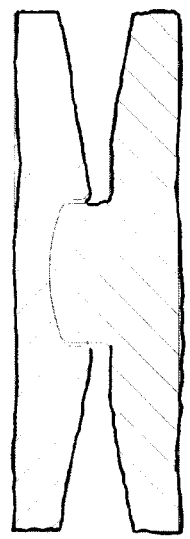 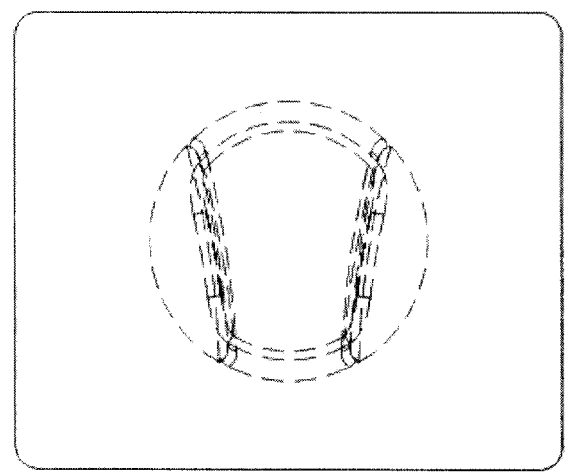
Fig. 6B
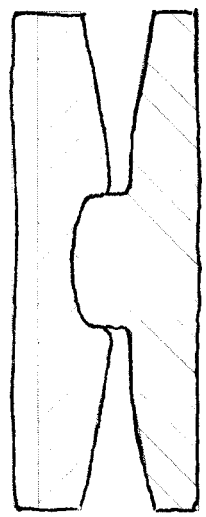 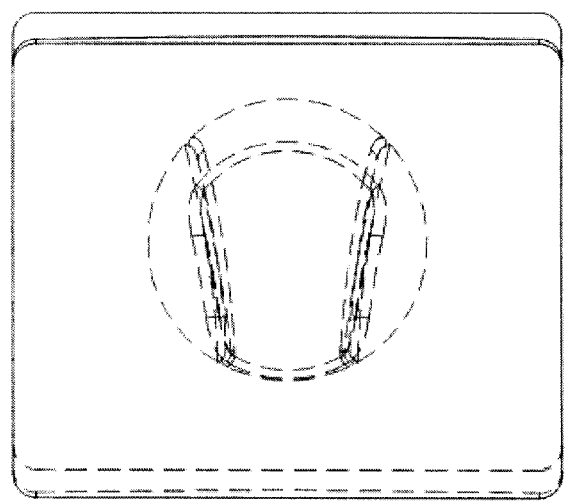
Fig. 6C

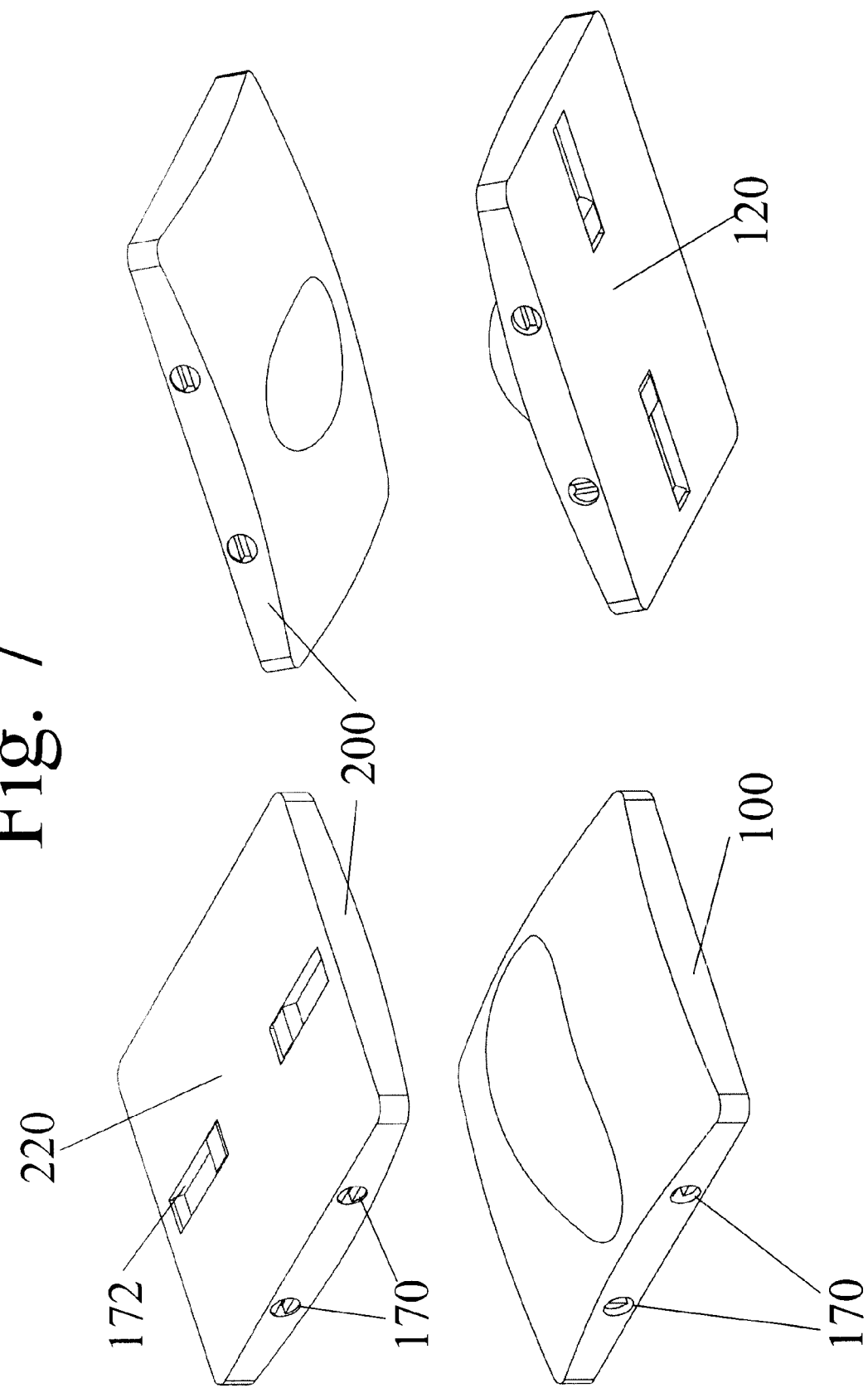

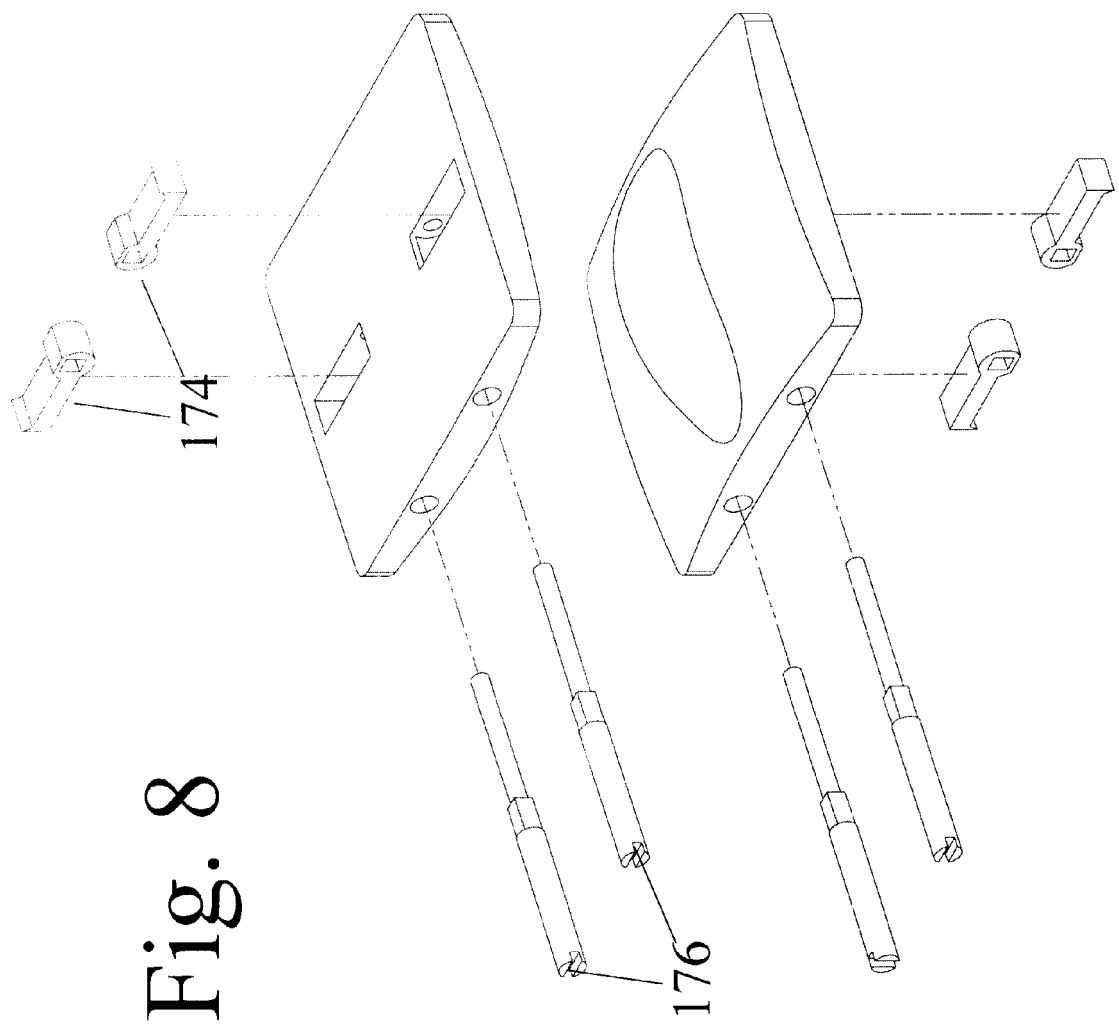

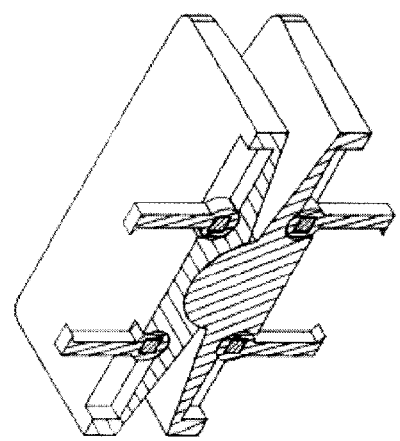
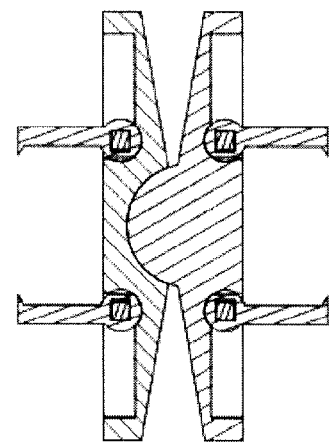
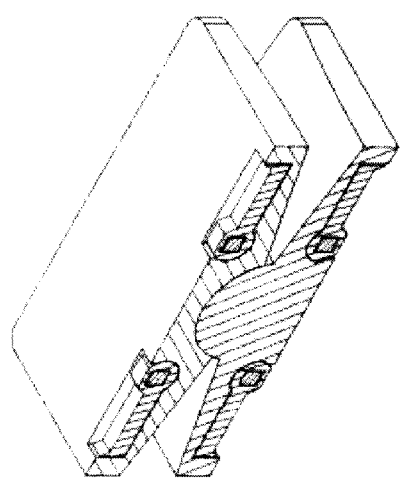
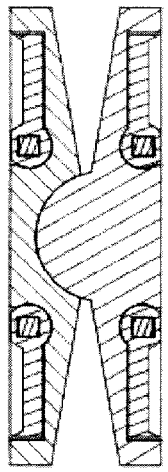
Fig. 9A
Fig. 9B

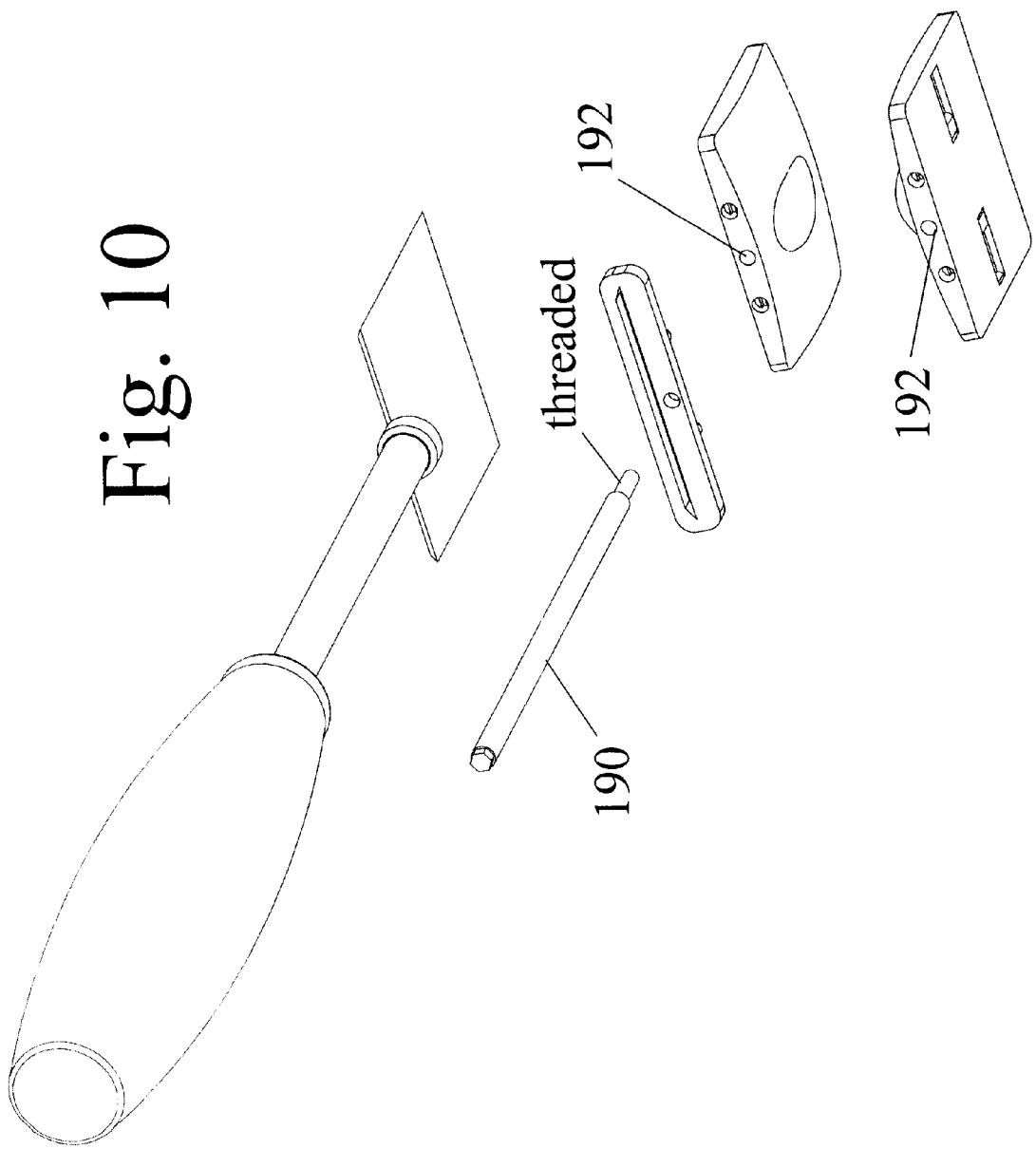

INTER-VERTEBRAL DISC PROSTHESIS WITH VARIABLE ROTATIONAL STOP AND METHODS OF USE

REFERENCE TO PRIORITY DOCUMENT

This application claims priority of co-pending U.S. Provisional Patent Application Ser. No. 60/793,790 filed Apr. 22, 2006. Priority of the aforementioned filing date is hereby claimed and the disclosure of the Provisional Patent Application is hereby incorporated by reference in its entirety.

BACKGROUND

Pain from degenerative spine disease is a major health problem in the industrialized world and the surgical treatment of spinal pathology is an evolving discipline. The traditional surgical treatment of a degenerating and painful inter-vertebral disc has been the complete immobilization and bony fusion of the involved spinal segment. An extensive array of surgical techniques and implantable devices have been formulated to accomplish this goal.

The growing experience with spinal fusion has shed light on the long-term consequences of vertebral immobilization. It is now accepted that fusion of a specific spinal level will increase the load on, and the rate of degeneration of, the spinal segments immediately above and below the fused level. As the number of spinal fusion operations have increased, so have the number of patients who require extension of their fusion to the adjacent, degenerating levels. The second procedure necessitates re-dissection through the prior operative field and carries significantly greater risk than the initial procedure while providing a reduced probability of pain relief. Further, extension of the fusion will increase the load on the motion segments that now lie at either end of the fusion construct and will accelerate the rate of degeneration at those levels. Thus, spinal fusion begets additional, future fusion surgery.

There is a growing recognition that segmental spinal fusion and complete immobilization is an inadequate solution to degenerative disc disease. Replacement of the degenerated and painful disc with a mobile prosthesis is a more intuitive and rational treatment option. This approach would permit preservation of spinal mobility in many patients with degenerative disc disease. Eventually, the degenerative process will progress sufficiently so that motion preservation with a mobile prosthesis is longer possible. Fusion and complete segmental immobilization is then reserved for those patients with advanced degenerative disease where the spinal segment is beyond surgical restoration.

U.S. Pat. Nos. 4,759,769; 4,997,432; 5,674,294; 5,674,296; 5,676,701; 5,888,226; 6,001,130; 6,019,792; 6,162,252; 6,348,071; 6,368,350; 6,419,706; 6,520,996; 6,540,785; 6,607,558; 6,645,249; 6,673,113; 6,749,635 and many others have illustrated various artificial disc prosthesis. Despite the large number of proposed designs, several issues remain poorly addressed.

Each spinal motion segment is composed of two adjacent vertebras and the articulations between them. These articulations include the anteriorly positioned inter-vertebral disc and the two posteriorly positioned facet joints. In the transfer of force between adjacent vertebral bodies, the inter-vertebral disc caries approximately 80% of the load while the remaining 20% is borne by the facet joints. A predominate function of the facet joints is to limit the extent of rotation and forward translation between the adjacent bones.

Since the articulation between adjacent vertebral bones is composed of the inter-vertebral disc and two facet joints, any attempt at restoration of vertebral motion must address all three components of the articulation. Replacement of the painful disc with an artificial prosthesis will restore a more full range of motion to the segment and those patients with extensive degenerative disease of the facet joints will experience an increase in facet joint pain after artificial disc implantation because of the increased motion. For this reason, artificial disc placement is contraindicated in those patients with significant facet joint disease. Similarly, those with healthy facet joints at the time of implantation will develop pain as these joints degenerate over time. In fact, the rate of facet joint degeneration and the subsequent development of pain are emerging as major determinates of the clinical success of artificial disc replacement. That is, patient who undergoes artificial disc replacement to treat back pain will have re-emergence of the pain symptoms as the facet joints degenerate and the rate of joint degeneration will determine the time till symptom recurrence. Since the useful life of the prosthesis greatly exceeds the life expectancy of the degenerating facet joint, the rate of joint degeneration becomes the true determinate of the pain-free interval that resides between the time of prosthesis implantation and the time of pain recurrence. The pain-free interval is a prominent statistic in the over-all determination of clinical success of these operations.

The design of the implanted disc prosthesis can significantly influence the rate of facet joint degeneration. As expected, a disc prosthesis that significantly loads the facet joint will accelerate the rate of joint degeneration and shorten the pain-free interval. Biomechanical studies have shown that the stress forces inside the facet joints tend to be highest when rotational forces are applied to the motion segment. Prosthetic discs that increase the extent of rotational freedom necessarily increase the load on the facet joints.

SUMMARY

Disclosed are artificial disc prostheses that provide a variable rotational stop will be disclosed. These devices replicate the motion characteristics of the healthy spine and minimize the stress loads on the facet joints. Unique methods of prosthesis attachment onto the vertebral bones are also disclosed.

In one aspect, there is disclosed a prosthesis for implantation into a disc space between two vertebral bodies of a spine, the prosthesis comprising: a first member adapted to couple to a first vertebral body and a second member adapted to couple to a second vertebral body wherein the first member and the second member have a permitted range of rotational motion with respect to one another and wherein the amount of permitted rotation of the first member relative to the second member is dependant on the extent of flexion and extension of the spine.

In another aspect, there is disclosed a prosthesis for implantation into a disc space between two vertebral bodies of a spine, the prosthesis comprising: a first member adapted to couple to a first vertebral body and a second member adapted to couple to a second vertebral body wherein the first and second members replicates the natural movement of the spine by allowing a progressively greater range of rotational movement with progressive flexion of the prosthesis members and lesser range of rotational movement with progressive extension of the prosthesis members.

In another aspect, there is disclosed a method of treating the spine, comprising: implanting a prosthesis in a disc space between a pair of vertebral bodies such that a first member of the prosthesis is attached to a first vertebral body and a second member of the prosthesis is attached to a second vertebral body wherein the prosthesis replicates the natural movement of the spine by allowing a progressively greater range of rotational movement with progressive flexion of the prosthesis members and lesser range of rotational movement with progressive extension of the prosthesis members.

In another aspect, there is disclosed a prosthesis for implantation into a disc space between two vertebral bodies of a spine, the prosthesis comprising: a first member adapted to couple to a first vertebral body; a second member adapted to couple to a second vertebral body; and at least one anchor member rotatably attached to the first member, wherein the anchor member extends from a non-deployed position wherein the anchor member is positioned within the first member, to a deployed position wherein the anchor member engages an adjacent bone structure to secure the prosthesis to the bone structure.

In another aspect, there is disclosed a method of securing a prosthesis to the spine, comprising: positioning the prosthesis in a disc space between a pair of vertebral bodies; and causing an anchor member to deploy outwardly from at least a portion of the implant such that the anchor member attaches to an adjacent bone structure, wherein the anchor member can be undeployed to dis-attach the anchor member from the bone structure.

Other features and advantages will be apparent from the following description of various embodiments, which illustrate, by way of example, the principles of the disclosed devices and methods.

BRIEF DESCRIPTION OF THE DRAWINGS

FIG. 1 shows perspective views of a prosthesis for implantation into a spine.

FIG. 3 shows top and side views of the prosthesis.

FIG. 4 shows the prosthesis in various states of motion.

FIGS. 5 and 6A-6C show another embodiment of a prosthesis.

FIG. 7 shows perspective views of a spinal prosthesis having a bone fixation feature.

FIG. 8 shows an exploded view of the spinal prosthesis of FIG. 7.

FIGS. 9A and 9B show the spinal prosthesis of FIG. 7 with anchor members in undeployed and deployed states.

FIGS. 10-12 show various views of a device for removing the prosthesis from the spine.

DETAILED DESCRIPTION

Figure 2:
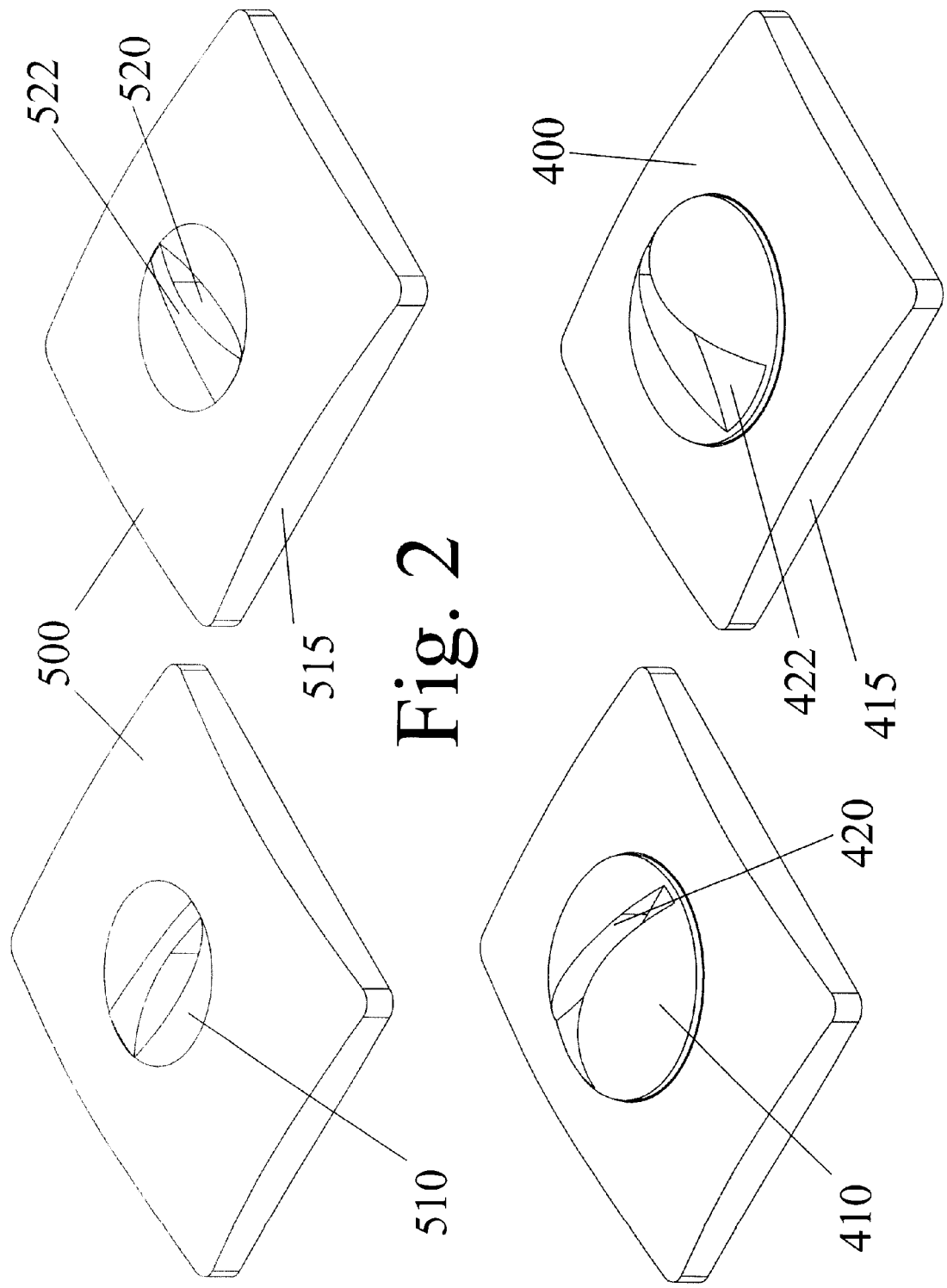
FIG. 2 shows individual members of the prosthesis of FIG. 1.

FIGS. 1 and 2 illustrate a prosthesis with a rotational bearing surface, such as a ball-in-socket bearing surface. The prosthesis is sized and shaped to be positioned within the disc space between a pair of spinal segments such as within a spine of a vertebral mammal. The natural spine is anatomically limited in range of rotational motion and the extent of allowable rotation varies with the amount of vertebral flexion. That is, the range of rotational movement (relative to the longitudinal axis of the spine) between two vertebral bodies is greatest when these vertebrae are in relative flexion. In contrast, the range of rotational movement between adjacent vertebrae is least when the vertebral bodies are in extension. The present embodiment replicates the natural spine by allowing a progressively greater range of rotational movement with progressive flexion of the prosthesis members.

In a first embodiment, the prosthesis has member 400 with spherical extension 410 and member 500 with spherical indention 510. The members 400 and 500 each have a flat or contoured outer surface (opposite the extension 410 or indentation 510) that is adapted to abut a portion of a spinal segment adjacent the disc space. The prosthesis can have bone attachment features, such as anchors, that are configured to secure the device to the bone. The bone attachment features are not shown in the figures for diagrammatic simplicity. Surfaces 415 and 515 are preferably the anterior surfaces of members 400 and 500, respectively.

In an assembled state, the indention 420 is placed in the mid-sagittal plane of extension 410 and has surface 422 at its bottom. Corresponding protrusion 520 is found in the mid-sagittal plane of indentation 510 and has surface 522 at its top. FIG. 3 shows the prosthesis in an assembled state. As shown in the sectional views of FIG. 3, surfaces 422 and 522 never abut in the assembled prosthesis so that the movement characteristics of the device are the governed by the interactions of spherical surfaces 410 and 510. That is, the spherical surfaces abut one another and provide bearing surfaces for the two members.

The indentation 40 and the protrusion 520 have a relative size and shape that is adapted to provided a limited extent of rotation of the first member relative to the second member. The interaction of indentation 420 and protrusion 520 limits the extent of rotation permitted about a central vertical axis that corresponds to the longitudinal axis of the spine when the prosthesis is implanted in the spine. Further, the amount of permitted rotation of the first member relative to the second member is dependant on the extent of flexion/extension. In specific, the extent of rotational freedom is greater in flexion and lesser in extension. Since the facet joints experience greater load with rotation and with extension, the prosthesis progressively limits rotation as the motion segment is placed into extension. This feature advantageously eliminates the cumulative load effects of both extension and rotation on the facet joints.

FIG. 4 shows the prosthesis in an extension (A) position, a neutral (B) position, and a flexion (C) position. In extension, the outer side walls of protrusion 520 are in apposition with the inner side walls of indentation of 420 so that little rotation is permitted. This is because the space between the outer side walls of protrusion 520 and the inner side walls of indentation 420 is limited when the prosthesis is in the extension. Thus, there is relatively little play so as to limit the amount of allowable rotation. It should be appreciated that in actual use, the members 400 and 500 would each be attached to a respective vertebral body (spinal segment) such that the range of motion would of the prosthesis would also apply to the attached vertebral bodies.

With reference still to FIG. 4, in the neutral position, a greater clearance exists between the walls of protrusion 520 and indentation 420 thereby allowing more rotational freedom. Thus, when the spine and the attached prosthesis are in the neutral position, the prosthesis permits a greater amount of rotational freedom than if the spine is in extension. This is because there is a greater amount of play between the walls of protrusion 520 and indentation 420. Finally, in flexion, maximal clearance exists between the interacting walls and an even greater amount of rotation is permitted. Thus, when the spine and the attached prosthesis are in the flexion, the prosthesis permits a greater amount of rotational freedom than if the spine is in extension and in the neutral position. As illustrated, this feature advantageously provides a progressive limit to rotational movement as the device is placed into extension.

Figure 5:
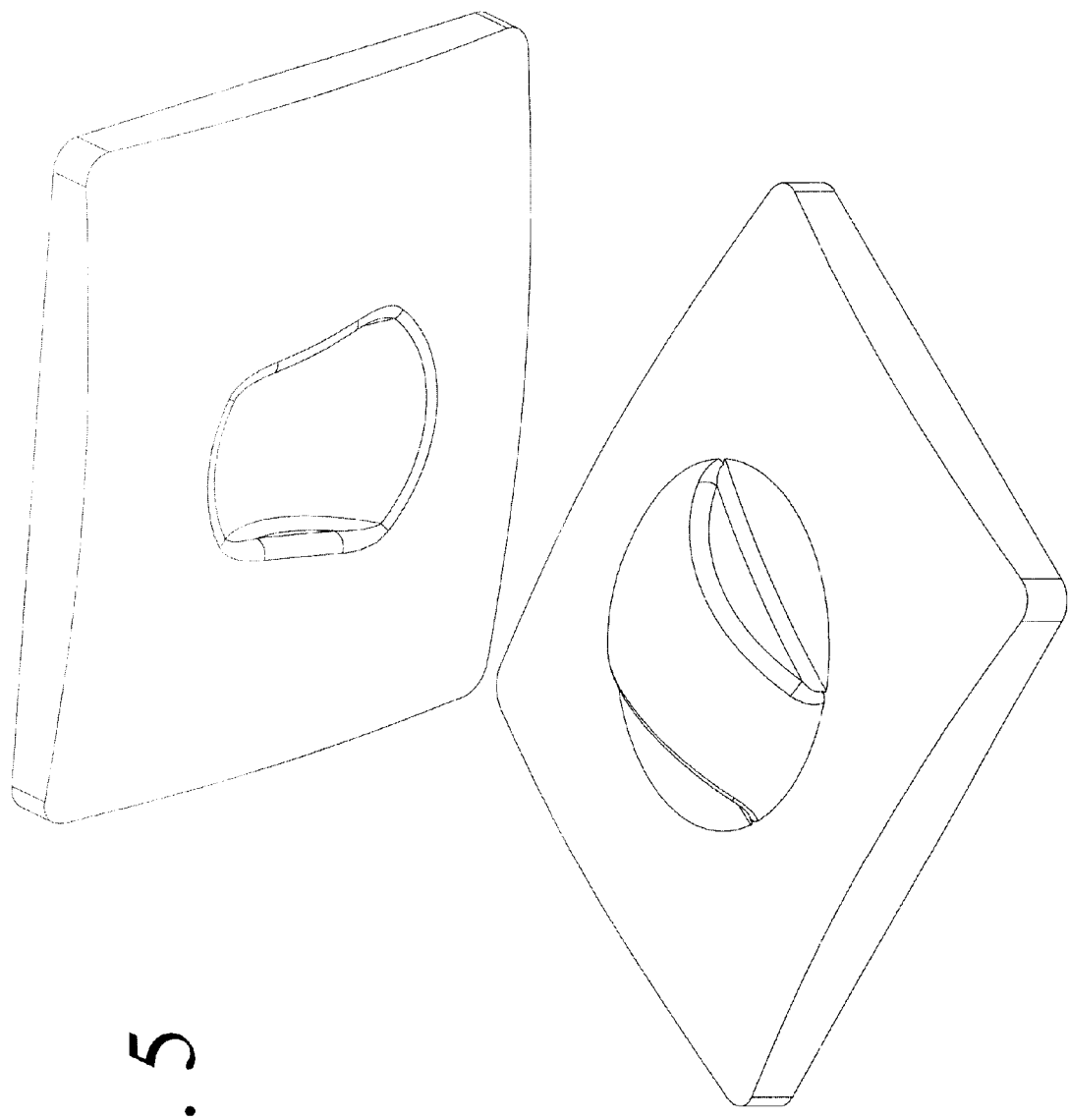

FIGS. 5 and 6 illustrate an additional device embodiment with a variable rotation constraint. Instead of a central rotational stop, this embodiment contains complimentary side protrusions/indentations that limit the extent of rotation. As shown in FIG. 6, the range of rotation permitted is greater in flexion than it is in extension.

Improved Device Fixation

FIG. 7 shows perspective views of a spinal prosthesis having a bone fixation feature. FIG. 8 shows an exploded view of the spinal prosthesis. The prosthesis has members 100 and 200 that mate with one another. The prosthesis is adapted to be positioned in a disc space between a pair of vertebral bodies. In one embodiment, bore holes 170 on the anterior surface of each of members 100 and 200 at least partially contain a bone attachment feature. Cavities 172 are situated within each of members 100 and 200 and contain rotational member 174. FIG. 8 shows the disassembled components. Elongated members 176 reside within bores 170 and interact with rotational members 174 so as to rotate them about the central axis of member 176.

FIG. 9A shows the prosthesis of FIG. 7 in an assembled state prior to deployment of fixation members. With implantation, the prosthesis is inserted into the evacuated disc space with each member 174 (the fixation members) completely contained within respective cavity 172, as shown in FIG. 9A. FIG. 9B shows the prosthesis in an assembled state prior with fixation members in a deployed state. That is, the fixation members 174 have been rotated outwardly from the members 100 and 200 such that the fixation members extend outwardly therefrom. After the prosthesis is correctly positioned in the disc space, a tool is used to engage the elongated members 176, which are then actuated, such as by rotation, so as to rotate the attached fixation members 174. The fixation members engage the adjacent bone and lock the prosthesis onto the adjacent bone (FIG. 9B). This feature permits instantaneous fixation of the prosthesis onto the adjacent bone and this fixation is reversible. That is, rotation of members 174 back into the confines of cavities 172 permits disengagement of the prosthesis from the surrounding bone.

As an additional feature, surfaces 220 and 120 may be made with porous ingrowth surfaces (such as titanium wire mesh, plasma-sprayed titanium, tantalum, porous CoCr, and the like), provided with a bioactive coating, made using tantalum, and/or helical rosette carbon nanotubes (or other carbon nanotube-based coating and the like) or any other appropriate method/coating that would promote bone in-growth and/or establish a mineralized connection between the bone and the implant.

Figure 11:
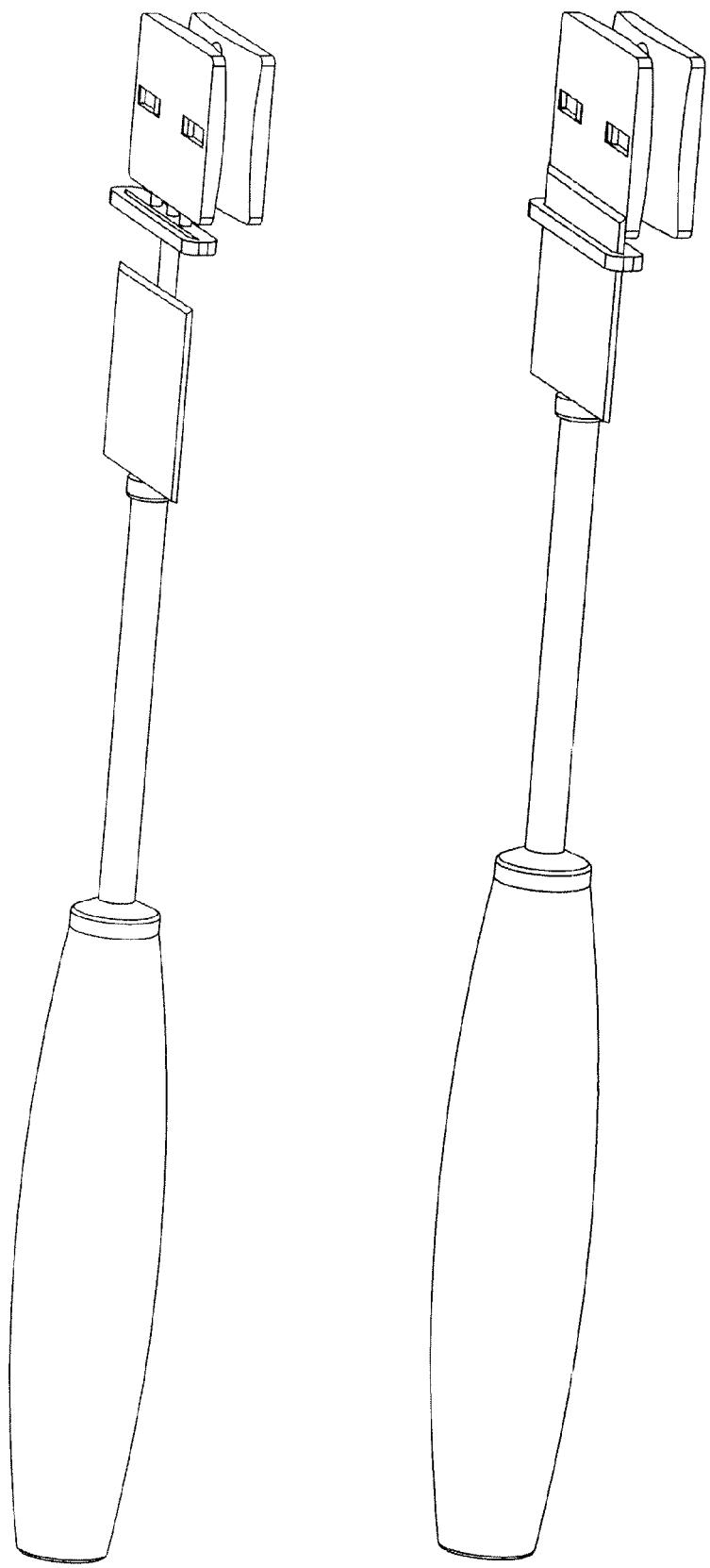
Figure 12:
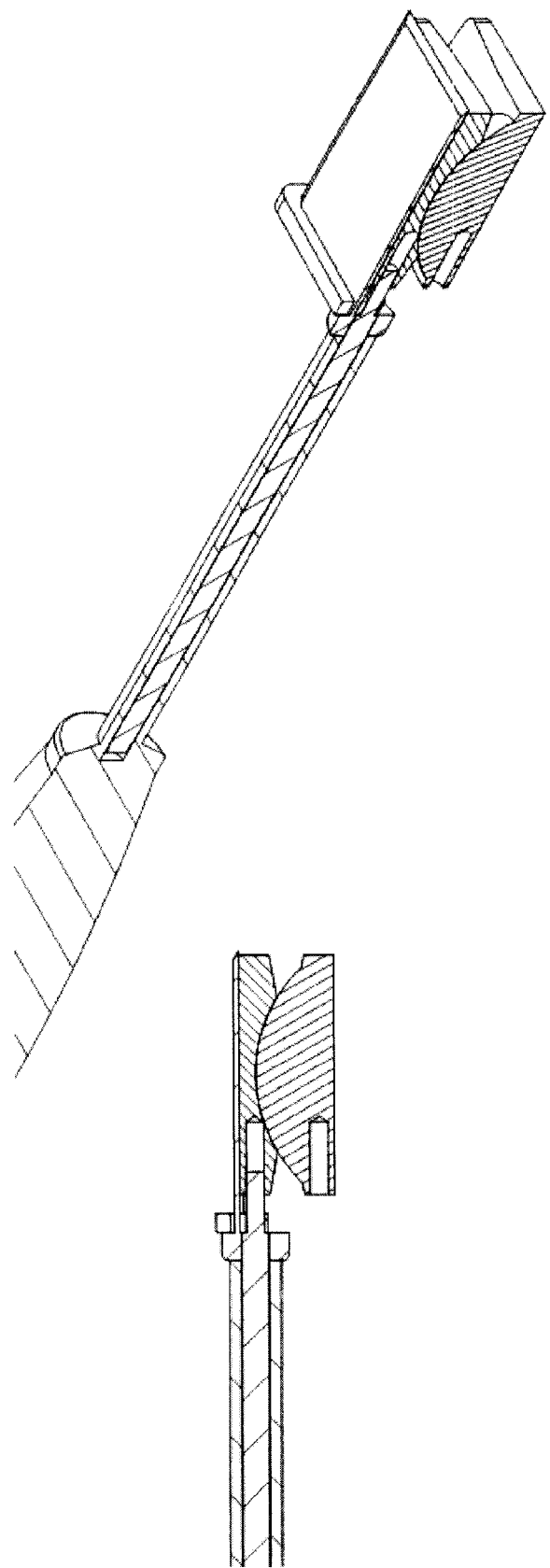

FIGS. 10-12 show various views of a device for removing the prosthesis from the spine. On prosthesis removal, an elongated threaded member 190 is used to attach a chisel guide onto the prosthesis using threaded bore 192. That is, the threaded member 190 mates with the threaded bore 192. The guide is used to position a bone-cutting chisel and break the attachment between the prosthesis and adjacent bone. The components are illustrated in FIG. 10. FIG. 11 shows the chisel advancing onto the superior surface of the implant and separating it from the adjacent bone. FIG. 12 shows a cross-sectional view of the fully advanced chisel and illustrates its relationship to the guide and member 190. Alternatively, a chisel guide/interaction feature may be placed directly onto the implant surface (not shown).

Any of the embodiments disclosed in this application and/or their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, the prosthesis surface(s) that are adjacent to bone may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the illustrated embodiments and/or any component can also be entirely or partially made of a shape memory material or other deformable material.

The shown embodiments are illustrative and do not limit the scope of the invention. At a minimum, additional embodiments of the present invention can be created by one of ordinary skill using various combinations of the embodiments illustrated herein. It is understood that various modifications may be made without departing from the spirit and scope of the claims. Accordingly, other embodiments are within the scope of the following claims.

What is claimed is:

1. An orthopedic implant configured to be positioned within an intervertebral disc space between a first vertebral bone and an adjacent second vertebral bone, comprising:
   a first implant member configured to extend along a longitudinal axis from an anterior surface to a posterior end, the first implant member comprising a bone abutment surface configured to abut a surface of the first vertebral bone, and a first bearing configured to articulate with a bearing surface of a second implant member;
   an elongated member configured to extend posteriorly from an aperture of the anterior surface of the first implant member and in the direction of the longitudinal axis, the elongated member being coupled to a proximal aspect of at least one bone fixation member, the bone fixation member configured to extend to a distal segment along a first axis and configured to rotate in a curvilinear trajectory that is centered about the longitudinal axis, the first axis comprising a different axis than the longitudinal axis;
   a bone fixation member comprising a distal end configured to project from a distal aspect in a direction of a tangent to the curvilinear trajectory, the distal end being further configured to advance into the first vertebral bone when rotated in a direction of the distal end, and the rotated bone fixation member being separated from simultaneous anchor into each of the first and the second vertebral bones; and
   a second implant member comprising a bone abutment surface configured to abut a surface of the second vertebral bone, and a first bearing configured to articulate with the first bearing surface of the first implant member;
   wherein the articulation maintains motion between the first and second vertebral bones.

2. An orthopedic implant as in claim 1, wherein the first axis forms a radial axis of the curvilinear trajectory.

3. An orthopedic implant as in claim 1, wherein the distal end of the bone fixation member is tapered.

4. An orthopedic implant as in claim 1, wherein a proximal aspect of the elongated member is configured to receive a tool capable of imparting a rotational force onto the elongated member.

5. An orthopedic implant as in claim 1, wherein the bone fixation member is configured to reversibly transition from a first rotational position to a second rotational position.

6. An orthopedic implant as in claim 5, wherein the bone fixation member is substantially contained within the first member when in the first rotational position.

7. An orthopedic implant as in claim 5, wherein the distal end of the bone fixation member is substantially exterior to the first bone abutment surface when in the second rotational position.

8. An orthopedic implant as in claim 7, wherein the bone fixation member enhances implant fixation onto at least one of the first or second vertebral bones when in the second rotational position.

9. An orthopedic implant as in claim 1, wherein the second implant member further comprises a second elongated member configured to extend posteriorly in a direction of a longitudinal axis and from an aperture of an anterior surface, the second elongated member being coupled to a proximal aspect of the bone fixation member.

10. An orthopedic implant as in claim 1, wherein at least a segment of the implant is manufactured from a metallic alloy.

11. An orthopedic implant as in claim 10, wherein the metallic alloy is at least partially comprised of Titanium.

12. An orthopedic implant as in claim 1, wherein at least a segment of the implant is manufactured from a plastic material.

13. An orthopedic device configured to be at least partially implanted within an intervertebral disc space between a first and a second vertebral bone, comprising:
   a first device member extending along a longitudinal axis from an anterior surface to a posterior end, and comprising:
      a bone abutment surface configured to abut a surface of the first vertebral bone; and
      an opposing bearing surface configured to movably articulate with a bearing surface of a second device member;
   a second device member comprising:
      an anterior surface;
      a posterior end;
      a bone abutment surface configured to abut the second vertebral bone; and
      an opposing bearing surface configured to movably articulate with the bearing surface of the first device member and to at least partially replace the movement of a natural disc; and
   a bone fixation mechanism comprising:
      an elongated member at least partially contained within the first device member and extending along a central axis; and
      a bone fixation member coupled to the elongated member at a proximal aspect and extending therefrom along a first axis that diverges from the central axis;
   wherein the bone fixation member further comprises a distal segment configured to rotate in a curvilinear trajectory about the central axis and a distal end configured to divergently project away from the first axis and along a direction of the curvilinear trajectory;
   wherein rotation of the elongated member advances the distal end of the bone fixation member into the abutted surface of the first vertebral bone; and
   wherein the bone fixation mechanism is separated from simultaneous advancement into each of the first and the second vertebral bones.

14. An orthopedic device as in claim 13, wherein the first axis comprises a radial axis to the curvilinear trajectory.

15. An orthopedic device as in claim 13, wherein the distal end of the bone fixation member is at least partly tapered.

16. An orthopedic device as in claim 13, wherein the bone fixation member is configured to reversibly transition from a first rotational position to a second rational position via a rotational force supplied by a tool received within a proximal aspect of the elongated member.

17. An orthopedic device as in claim 16, wherein in the first rotational position, the bone fixation member is substantially contained within the first member, and in the second rotational position, the distal end of the bone fixation member is substantially exterior to the first bone abutment surface.

18. An orthopedic device as in claim 16, wherein in the first rotational position, the bone fixation member is substantially contained within the first member, and in the second rotational position, the bone fixation member enhances implant fixation onto at least one of the first or second vertebral bones.

19. An orthopedic device as in claim 13, wherein the second device member further comprises a second elongated member configured to extend posteriorly in a direction of a longitudinal axis and from an aperture of an anterior surface, the second elongated member being coupled to a proximal aspect of the bone fixation member.

20. An orthopedic implant configured to be implanted within a disc space between first and second vertebral bones, the implant comprising:
   a first implant member configured to extend along a longitudinal axis from an anterior surface to a posterior end and comprising a surface configured to abut the first vertebral bone;
   an elongated member configured to extend posteriorly from an aperture of the anterior surface of the first implant member and in the direction of the longitudinal axis;
   a bone fixation member configured to:
      couple at a proximal aspect thereof to the elongated member;
      extend to a distal segment along a first axis, the first axis comprising a different axis than the longitudinal axis;
      rotate in a curvilinear trajectory that is centered about the longitudinal axis; and
      project a distal tip from a distal aspect thereof in a direction of a tangent to the curvilinear trajectory, the distal tip configured to advance into the first vertebral bone upon rotation of the bone fixation member; and
   a second implant member comprising a surface configured to abut the second vertebral bone and a bearing configured to articulate with a respective bearing of the first implant member;
   wherein the first and second implant members are configured to maintain motion between the first and second vertebral bones during articulation; and
   wherein the bone fixation member is separated from simultaneous anchoring into each of the first and the second vertebral bones.

* * * * *

UNITED STATES PATENT AND TRADEMARK OFFICE
CERTIFICATE OF CORRECTION

Page 1 of 1

PATENT NO.         : 8,303,660 B1
APPLICATION NO.    : 11/739053
DATED              : November 6, 2012
INVENTOR(S)        : Samy Abdou It is certified that error appears in the above-identified patent and that said Letters Patent is hereby corrected as shown below:

Claims

Col. 8, lines 11-14, claim 16

"16. An orthopedic device as in claim 13, wherein the bone fixation member is configured to reversibly transition from a first rotational position to a second rational position via a rotational force supplied by a tool received within a proximal aspect of the elongated member."

Should Read:

--16. An orthopedic device as in claim 13, wherein the bone fixation member is configured to reversibly transition from a first rotational position to a second rotational position via a rotational force supplied by a tool received within a proximal aspect of the elongated member.--

Signed and Sealed this
Twenty-seventh Day of October, 2015

Michelle K. Lee
*Director of the United States Patent and Trademark Office*